United States Patent
Sano et al.

(10) Patent No.: US 6,736,779 B1
(45) Date of Patent: May 18, 2004

(54) ULTRASONIC PROBE AND ULTRASONIC DIAGNOSTIC DEVICE COMPRISING THE SAME

(75) Inventors: Shuzo Sano, Kashiwa (JP); Yutaka Sato, Kashiwa (JP); Jun Kubota, Nagareyama (JP); Shinji Kishimoto, Mitsukaido (JP); Ryuichi Shinomura, Higashimatsuyama (JP); Satoshi Tamano, Kashiwa (JP); Takaya Osawa, Sugito-machi (JP); Yuichi Miwa, Kokubunnji (JP); Hiroshi Masuzawa, Kokubunnji (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 10/088,120

(22) PCT Filed: Sep. 13, 2000

(86) PCT No.: PCT/JP00/06266
§ 371 (c)(1),
(2), (4) Date: Jul. 10, 2002

(87) PCT Pub. No.: WO01/21072
PCT Pub. Date: Mar. 29, 2001

(30) Foreign Application Priority Data

Sep. 17, 1999 (JP) .......................................... 11/263033
Dec. 14, 1999 (JP) .......................................... 11/354601

(51) Int. Cl.$^7$ ................................................. A61B 8/00
(52) U.S. Cl. ...................................................... 600/447
(58) Field of Search ................................. 600/437, 443, 600/447, 459; 73/625–626; 310/334

(56) References Cited

U.S. PATENT DOCUMENTS

| | | | | | |
|---|---|---|---|---|---|
| 4,219,846 A | * | 8/1980 | Auphan | ...................... | 358/112 |
| 4,307,613 A | * | 12/1981 | Fox | .............................. | 73/626 |
| 4,641,660 A | * | 2/1987 | Bele | ........................... | 600/443 |
| 5,027,820 A | * | 7/1991 | Pesque | ....................... | 600/443 |
| 5,563,346 A | * | 10/1996 | Bartelt et al. | ................. | 73/626 |

* cited by examiner

Primary Examiner—Francis J. Jaworski
(74) Attorney, Agent, or Firm—Antonelli, Terry, Stout & Kraus, LLP

(57) ABSTRACT

An ultrasonic probe in which two-dimensional array transducer elements are arrayed convexly both in one direction of the two-dimensional array and in the direction perpendicular to the former direction relative to the direction where an ultrasonic wave is transmitted. By switching a transducer element selecting switch circuit provided near the transducer elements, the shape of the diameter of the probe for transmitting and receiving of ultrasound and the position of the diameter are arbitrarily determined. An ultrasonic diagnostic apparatus in which a fresnel ring is formed as an diameter by a control signal to a transducer element selecting switch circuit, the number of cables for connection between the probe and the main body is decreased by bundling the transducer elements in one ring and effecting the connection, the fresnel ring is moved every ultrasonic transmission/reception cycle by the control signal to the transducer element selection switching circuit, and an object is three-dimensionally scanned with an ultrasonic beam.

18 Claims, 8 Drawing Sheets

(a)

(b)

ULTRASONIC PROBE AND ULTRASONIC DIAGNOSTIC DEVICE COMPRISING THE SAME

FIELD OF THE INVENTION

This invention relates to a technique for three-dimensionally scanning with an ultrasonic beam in an object to be examined, particularly to a two-dimensional array ultrasonic probe being capable of three-dimensional scanning with an ultrasonic beam in the object by an electronic control and an ultrasonic diagnostic apparatus comprising it.

BACKGROUND

Recently an ultrasonic diagnostic apparatus that transmits and receives an ultrasonic beam with an ultrasonic probe and three-dimensionally scans in the object, and corrects a three-dimensional data from the object, and makes a three-dimensional image to supply for diagnosis is developing. In the first example of such apparatus, a three-dimensional image data is corrected by moving in parallel and mechanically on the surface of an object an ultrasonic probe arranged a plurality of transducer elements in one direction. And there is an apparatus that scanning of beam is performed with inclining consecutively contact angle of said probe to the object from one side to another without changing contact position between the probe and the object.

In addition, in the second example, 2D-array ultrasonic probe is composed with 64×64 elements arrayed in two-dimensional direction. An ultrasonic beam with gimlet shape is transmitted and received in or from interior of the object by using a specified transducers fixedly selected in said 2D arrangements, and a three-dimensional image data is corrected from the object to be examined. In addition, a two-dimensional probe is a probe that an arrangement of elements is expanded from one direction to two directions. For example it is disclosed in Ultrasonic Imaging 14, 213–233 (1992); IEEE Trans. UFFC 38, 100–108 (1991).

However, in these traditional ultrasonic diagnostic apparatus, in said first example, an ultrasonic probe and an ultrasonic diagnostic apparatus had to be large and heavy because a driving system for scanning an ultrasonic beam and moving a probe mechanically is necessary. Therefore, small and light two-dimensional probe is desired from an operator on operational view. In addition, a scanning range is basically restricted by said composition of driving system, so an arbitrary range can not be scanned. Furthermore, said mechanical scanning mechanism causes abrasion. So its life times are short.

In the second example, only the fixedly selected specified elements in two-dimensional array transducer elements are used for transmitting and receiving to scan electrically an ultrasonic beam with gimlet shape. So a region for correcting three-dimensional data was narrow. In addition, even element number used in transmitting and receiving is specified as a part of 64×64, but is necessary about 256. So number of cables connected to each element needs a lot. And if number of transducer element for transmitting and receiving ultrasound is increasing, number of beam forming circuit disposed on main body of diagnostic apparatus needs also a lot.

SUMMARY OF THE INVENTION

Thus in view of previously described subject, the first object of the present invention is to provide small and light ultrasonic probe that is able to three-dimensional scan with transmitting and receiving an ultrasonic beam to the object to be examined.

The second object of the present invention is to provide a two-dimensional array probe that is easy to contact to the surface of the object to be examined.

The third object of the present invention is to provide an ultrasonic probe that is able to three-dimensional scan to the object to be examined with an ultrasonic beam without using mechanical scanning mechanism such as previously described.

The fourth object of the present invention is to provide an ultrasonic probe that a three-dimensional image data can be acquired from wide range of the object to be examined.

The fifth object of the present invention is to reduce number of cable for connecting an ultrasonic probe and a main body of diagnostic apparatus, and to provide an ultrasonic diagnostic apparatus that an operator is not influenced by weight and hardness of cable when the operator operates said probe.

Furthermore, the sixth object of the present invention is to provide an ultrasonic diagnostic apparatus being capable of transmitting and receiving with a two-dimensional array probe and having a few beam forming circuits.

And the seventh object of the present invention is to provide an ultrasonic diagnostic apparatus being obtained good quality image and being capable of dynamic focusing with two-dimensional array probe.

In order to achieve said object, an ultrasonic probe in the first invention comprises plural number of transducer element for transmitting and receiving ultrasound arrayed in two-dimensional direction and correcting an ultrasonic signal. And said plural number of transducer element are arrayed with convex shape to transmitting direction in at least one direction or two directions, which two directions are perpendicular to each other. And in an ultrasonic probe having convex shape in two directions, the transducer arrangement in this two direction is preferable to apply radial arrangement in two directions, or one radial arrangement and one parallel arrangement.

In addition, an ultrasonic probe of the present invention has an element selecting switch circuit for selectively switching arbitrarily transducer elements for transmitting and receiving ultrasound in the neighborhood of said two-dimensional array transducer elements. An output line of said element selecting switch circuit is connected to each element of arrayed transducer and number of input lines is less than that of arrayed transducer.

In the probe of the present invention, an arbitrary transducer can be selected by controlling signal to said element selecting switch circuit. Accordingly diameter with arbitrary shape can be formed. In addition, this diameter can be moved by the controlling signal to element selecting switch circuit. Three-dimensional scanning to interior of the object is possible by this motion of diameter with ultrasonic beam.

In order to achieve said object, in the present invention a related invention to said ultrasonic probe as a specified invention is disclosed. An ultrasonic diagnostic apparatus in the related invention of the preset invention comprises an ultrasonic probe including a two-dimensional array probe having minute ultrasonic transducer elements, element selecting means for supplying data to select elements transmitting and receiving ultrasound from array transducer of said ultrasonic probe, means for supplying bundling data for bundling and connecting said selected transducer elements to plural number of group, means for transmitting ultrasound to the object with applying the predetermined transmitting delay time to said bundled transducer element groups, means for beam forming with receiving signals of said each bundled transducer group, means for image processing output signal of this beam forming means, and an image display means.

In this related invention, it is a characteristic that the transducers bundled to said plural number of group form fresnel ring having a concentric circle. And the ring is designed such that the difference between a maximum and a minimum distance, which is distance between transducer element in each ring forming said fresnel ring and ultrasonic focus point, is less than ⅛ wave length of ultrasound.

In said ultrasonic diagnostic apparatus, the form of said fresnel ring is not changed during an echo signal is received. And means for controlling said beam forming circuit corresponding to a received signal of each ring so as to move receiving focus point continuously on the center axis line of fresnel ring is comprised. Furthermore, said apparatus comprises means for changing form of said fresnel ring corresponding to the depth of receiving focus point, means for ultrasonic scanning the predetermined depth region in the object with each form of said fresnel ring, and means for composing an image from echo signal acquired at each depth region, necessarily.

Moreover an ultrasonic diagnostic apparatus of the related invention preferably comprises a two-dimensional array probe for transmitting and receiving ultrasound to the object, a main body of diagnostic apparatus for acquiring and displaying an ultrasonic image of diagnostic part in the interior of the object by using an ultrasonic signal corrected with this two-dimensional array probe, and data transmitting part for inputting and outputting a selecting data of transducer elements and said corrected ultrasonic signal from one direction to another between said two-dimensional array ultrasonic probe and said main body.

THE BEST MODE FOR CARRYING OUT THE INVENTION

Hereinafter an embodiment of the present invention will be described in detail referring to an attached figure. At first an embodiment of the ultrasonic probe of the present invention will be described.

Figure 1:
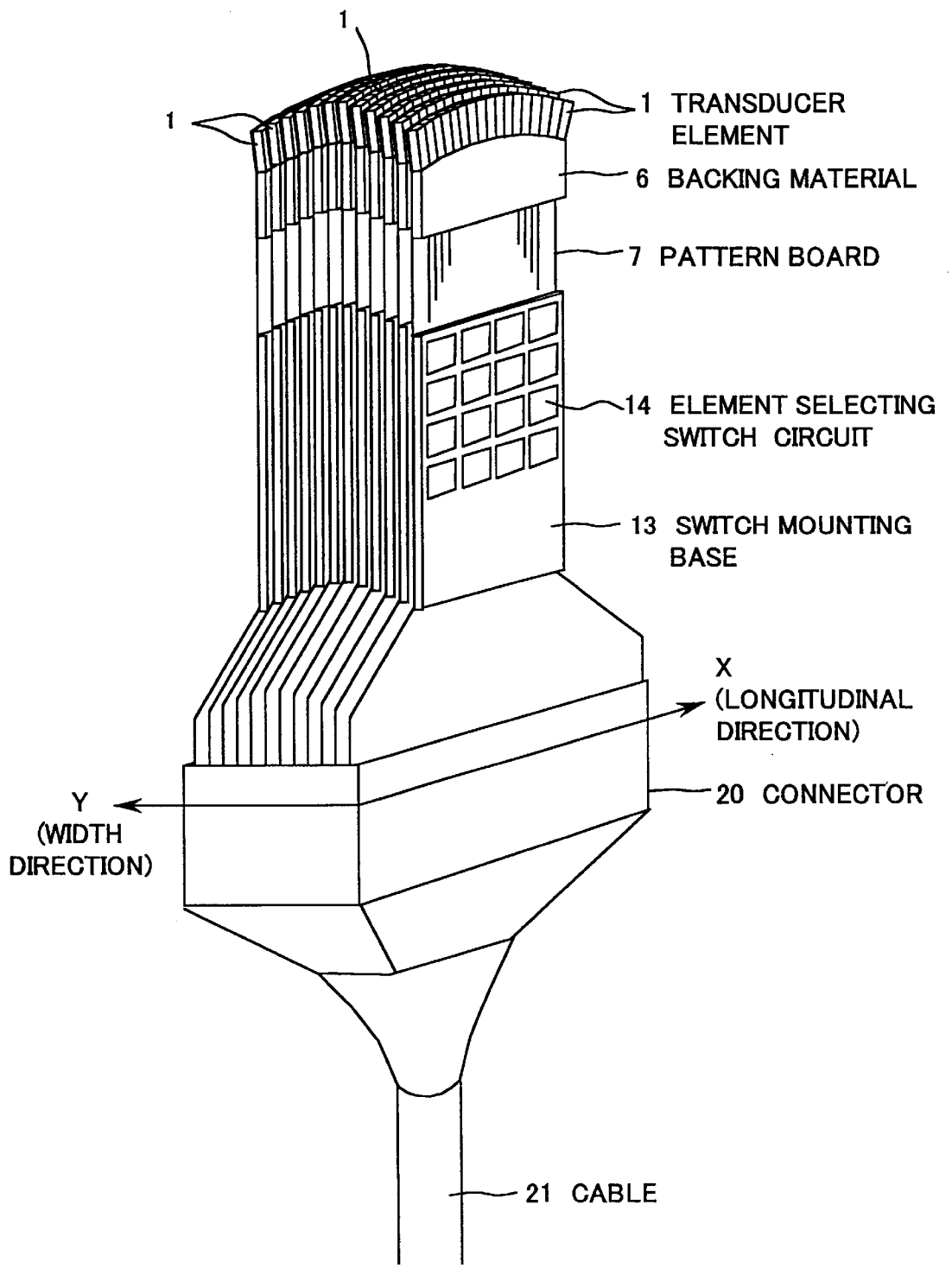
FIG. 1 is a perspective view showing an embodiment of an ultrasonic probe in a specific invention of the present invention for showing an interior structure of it.

FIG. 1 is a perspective view showing an embodiment of the ultrasonic probe of the present invention. This ultrasonic probe comprises plural number of transducer element arranged in two-dimensional direction for transmitting and receiving ultrasound to the object to be examined. And in this ultrasonic probe, a plurality of transducer elements 1, for example 12,448 elements, are arranged to longitudinal direction (x direction) and width direction (y direction) with 196×64 elements, or 6,244 elements are arranged to longitudinal direction (x direction) and width direction (y direction) with 128×48 elements. And, they are arrayed with a convex shape in the ultrasound transmitting direction to both directions, which are one direction (longitudinal direction) and another direction across it.

Circular angle formed with the transducer elements in the longitudinal direction X, for example 196 or 128 elements is about 68 degrees, and a circular radius forming an ultrasound transmitting and receiving face of transducer elements is 60 mm. And the circular angle formed with the transducer elements in the width direction Y, for example with 64 or 48 elements is about 48 degrees, and a circular radius in ultrasound transmitting and receiving face is 32 mm. And a three-dimensional scanning is possible within the field of view 68 degrees×48 degrees by ultrasonic beams.

Figure 2:
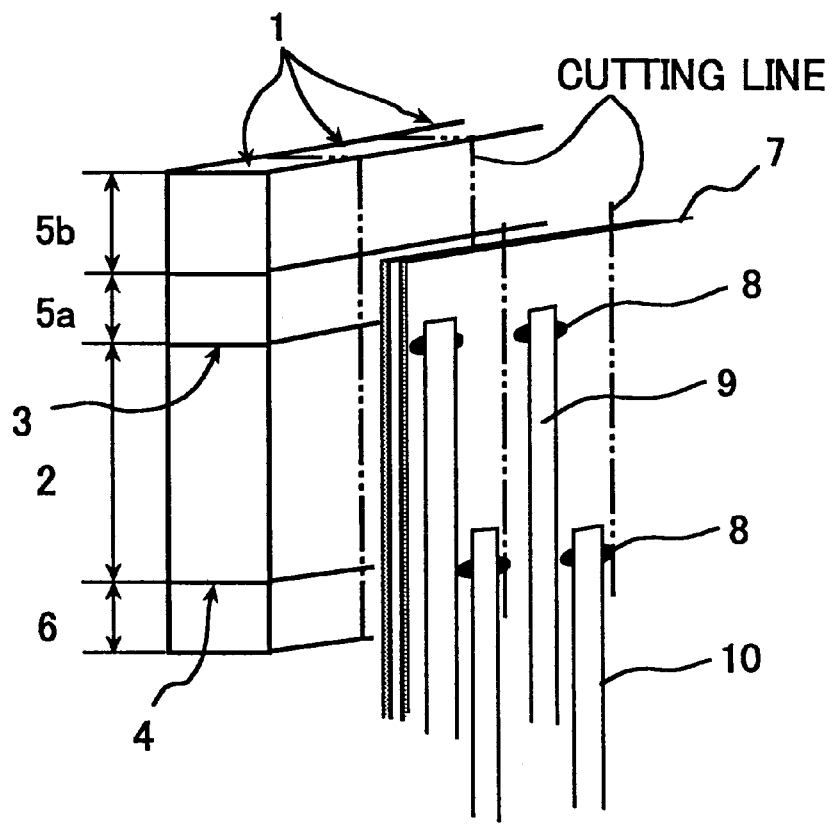
FIG. 2 is a perspective view showing structure of transducer elements, for example structure of one line in longitudinal direction.

Said transducer elements 1 transmit an ultrasound to the object and receive a reflection wave from the object. And they consist of a piezoelectric material for exchanging mutually between an electric signal and a mechanical vibration. One line structure of these transducer elements 1 in the longitudinal direction X is shown in FIG. 2. Ground electrode 3 is fixed on the top of piezoelectric material 2, and signal electrode 4 is fixed on the bottom of it. Furthermore, two matching layers (acoustic adjustment layer) 5a, 5b are fixed on the top of said ground electrode 3, sound attenuation material (backing material) 6 is fixed on the bottom of signal electrode 4.

As thus described piezoelectric material 2, in which matching layer 5a, 5b and backing material 6 is fixed on the top or the bottom of it, is previously cut to a thin plate. And pattern board 7 is fixed with solder to ground electrode 3 and signal electrode 4 to the exposed sides of it. On this pattern board 7, ground electrode pattern 9 and signal electrode pattern 10 are formed, and they are connected to said ground electrode 3 and signal electrode 4 through solder pad 8. And, in the condition that pattern board 7 is fixed as described above, each transducer element 1 is formed by cutting separately the whole piezoelectric material 2 with dicing saw along a cutting line 11 shown with a chain double-dashed line. In addition, it is preferable to cut separately the whole piezoelectric material 2 etc. along the cutting line 11 before solder fixing of pattern board 7, and to arrange transducer element 1 respectively in accordance with ground electrode pattern 9 and signal electrode pattern 10 of pattern board 7.

Figure 3:
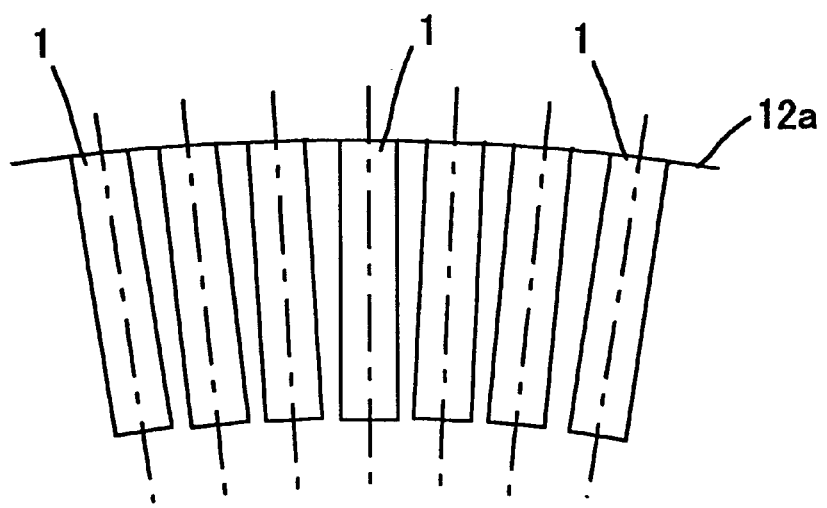
FIG. 3 shows plural number of transducer elements arranged in longitudinal direction in FIG. 1.

In FIG. 1, an arrangement of plural number of transducer element 1 arrayed in the longitudinal direction X is shown in FIG. 3. That is to say, in the longitudinal direction X, for example 192 transducer elements 1 are arrayed. And the top face of them is positioned along longitudinal arrangement orbit 12a. The transducer elements 1 are arrayed as a whole with circular convex and radial arrangement in the transmitting direction, which is called convex type in the field of the invention. In this embodiment, the center axis of each element 1 is radiated outward. And the ultrasonic transmitting and receiving face of each element 1 is arranged to the normal direction of longitudinal arrangement orbit 12a. Accordingly, high sensitivity direction of ultrasound transmitting and receiving of each element 1 is faced to the normal direction of longitudinal arrangement orbit 12a. So especially a signal receiving sensitivity in both ends of transducer array is improved.

Figure 4:
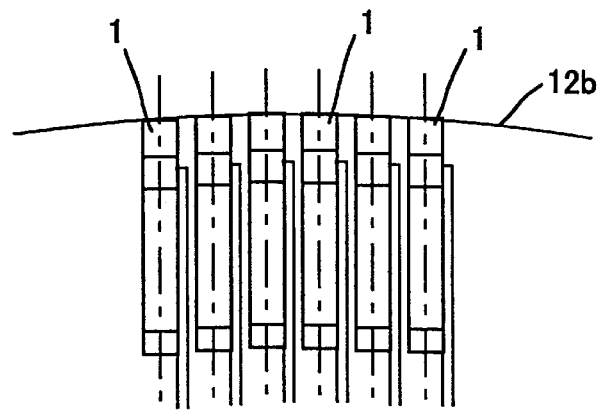
FIG. 4 shows plural number of transducer elements arranged in width direction in FIG. 1.

In addition, an arrangement of plural number of transducer element 1 arrayed in the width direction Y in FIG. 1 is shown in FIG. 4. That is to say, in the width direction Y for example 64 transducer elements 1 are arrayed as thus described. And the top face of them is positioned like a stairs along width arrangement orbit 12b. And they are arrayed with a circular convex type in the transmitting direction that is to say said convex type. In this embodiment, the center axis of each element 1 is arranged in parallel. Both ends of array 1 are arranged to be inclined with a certain degree to the normal direction of width arrangement orbit 12b. Therefore, the signal receiving sensitivity falls down a little at both ends of transducer array.

As previously described, a two-dimensional probe of the present invention is applied with the convex shape at both directions of longitudinal and width. Accordingly the fitness of probe on the surface of the object is improved.

Next, In FIG. 1, each transducer element is connected to element selecting switch circuit 14 on switch mounting base 13 through pattern board 7. This element selecting switch circuit 14 selects an arbitrarily transducer element for transmitting and receiving ultrasound. And they are connected respectively to each of said plural transducer elements on said two-dimensional array. That is to say in FIG. 5, n pieces of transducer element are arranged in the longitudinal direction X, and m pieces of transducer element in the width direction Y. And all of them are connected to element selecting switch 14a, for example composed of cross point switch. And in two-dimensional probe composed like these, the transducer elements for in actually transmitting and receiving ultrasound are selected arbitrarily by controlling said element selecting switch 14a through shift register 16 and parallel latch 17 and decoder 18 in the transducer array with a selecting data input from exterior element selecting data part 15.

Figure 5:
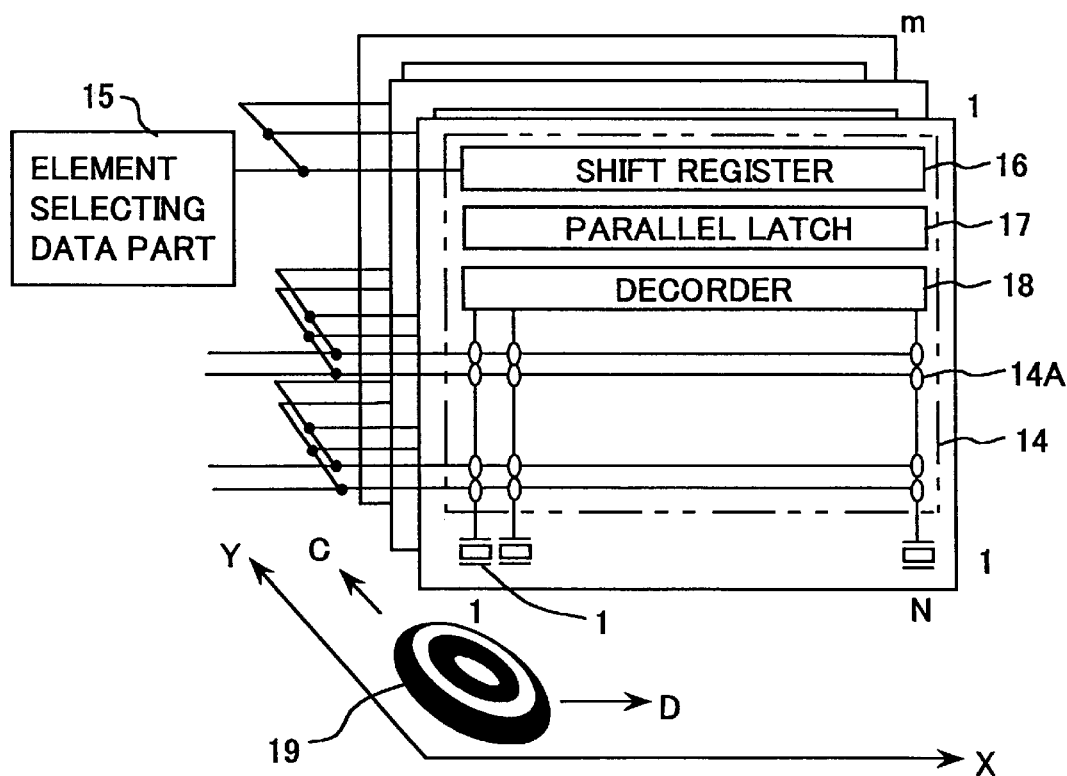
FIG. 5 is a view showing outline of element selecting switch circuit combined in a two-dimensional probe shown in FIG. 1.

And one example for forming an arbitrary shape diameter for ultrasound transmitting and receiving by selecting an arbitrary transducer element with the control of said element selecting switch circuit 14 is shown as follows. As shown in the bottom of FIG. 5, plural number of transducer element is selected from two-dimensional array of n pieces in the longitudinal direction (x direction) and m pieces in the width direction (y direction) by controlling of element selecting switch circuit 14. Those elements are selected with concentric circle for example, diameter 19 composed of a fresnel ring is formed to connect and bundle elements in the same ring. That is to say, it is possible to form a focusing beam by the fresnel ring with divided annular array. In addition, it is possible to form equally divided annular array and other type of arbitrary shape array. This fresnel ring, in which transducer elements are bundled with concentric circle, is disclosed in U.S. Pat. No. 4,219,846.

Furthermore, the two-dimensional probe of the present invention can transmit and receive an ultrasonic beam with continuously moving diameter 19, which composes of the fresnel ring, by controlling said element selecting switch circuits 14 at each repetition of the ultrasound transmitting and receiving to two directions of arrowed C and D as shown in FIG. 5 on the face of probe. And it can scan ultrasound beam at three-dimensional direction in certain range, and can get a three-dimensional image data. In addition the shape of said diameter 19 is not restricted to the fresnel ring, in which the transducer elements are bundled into a concentric circle, but it is possible to bundle into oval, rectangular, or other arbitrary shape, with changing transducer selecting switch circuit 14. In this case, ultrasonic beam focused with an arbitrary shape is transmitted and received from the diameter 19.

FIG. 1 will be referred to again. Code 21 shows a cable for connecting two-dimensional probe to the main body of an ultrasonic diagnostic apparatus being outside of the figure. And code 20 shows a connector for connecting the transducer elements of two-dimensional probe to this cable 21. By controlling said element selecting switch circuit 14 by control a device disposed in said main body through this cable 21 and connector 20, an arbitrary transducer element is selected to form an arbitrary form diameter for transmitting and receiving ultrasound. Focused ultrasound beam with an arbitrary shape can be transmitted and received from this diameter to scan three-dimensionally. Accordingly, in an ultrasonic probe of the present invention cable 21 is needed only at least the number of transducer element forming an arbitrary shape diameter for ultrasound transmitting and receiving and the number of signal line for supplying a transducer selecting data. Then the probe can be smaller and lighter.

Figure 6:
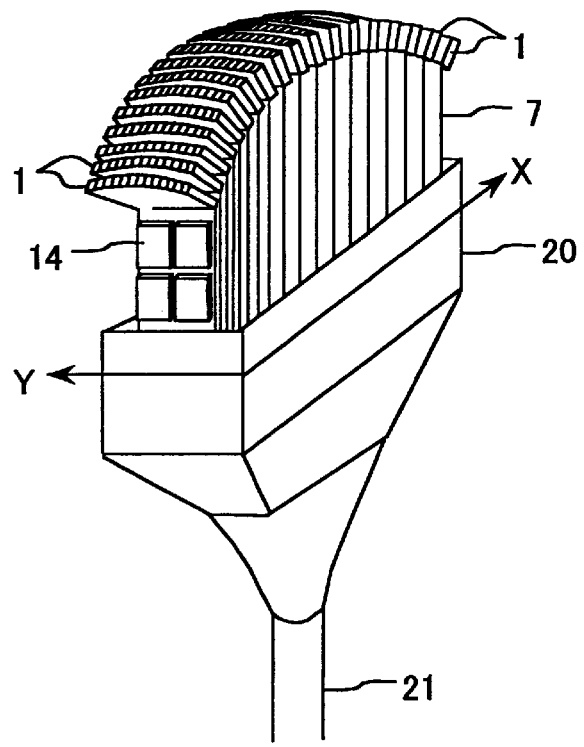
FIG. 6 is a perspective view showing modified example of a two-dimensional ultrasonic probe of the present invention for showing interior structure of it.

FIG. 6 is a perspective explanation view showing a modified example of the ultrasonic probe shown in FIG. 1, and a schematic view showing the interior structure of it. In this modified example plural number of transducer element 1 are arranged with a convex type, which is a circular convex shape in the longitudinal direction X as same as shown in FIG. 3 and a radial arrangement in an ultrasound transmitting direction. And they are also arranged in the width direction Y as same as shown in FIG. 3, a convex type.

In this probe of the modified example a high sensitivity direction of ultrasound transmitting and receiving of each element 1 is turned to the normal direction of longitudinal arrangement orbit 12a in the longitudinal direction X And a high sensitivity direction of ultrasound transmitting and receiving of each element 1 in width direction Y is turned to the normal direction of width arrangement orbit 12b. This arrangement is ideal to scan ultrasonic beam in the longitudinal direction X and the width direction Y Especially the receiving sensitivity on both ends of transducer array can be improved.

The two-dimensional probe of the present invention is composed as these. So plural number of transducer element is arranged with a circular convex shape in each of two directions being perpendicular to each other in the ultrasound transmitting direction. Accordingly the two-dimensional probe having a good contact with the surface of the object to be examined is provided. And, the fitness of probe to the object can be improved by the arrangement with convex shape at least one direction of two-dimensional array. So it is preferable to arrange as those.

And, an element selecting switch circuit for selecting an arbitrary transducer element transmitting and receiving ultrasound is disposed in the neighborhood of said two-dimensional array transducer elements. And an arbitrary transducer element can be selected by controlling on and off of this element selecting switch circuit, and plural number of transducer element can be connected in common (bundled connection). Therefore the number of cable for connecting the main body and the probe can be reduced. Accordingly an examiner's load for scanning the probe can be reduced.

Figure 7:
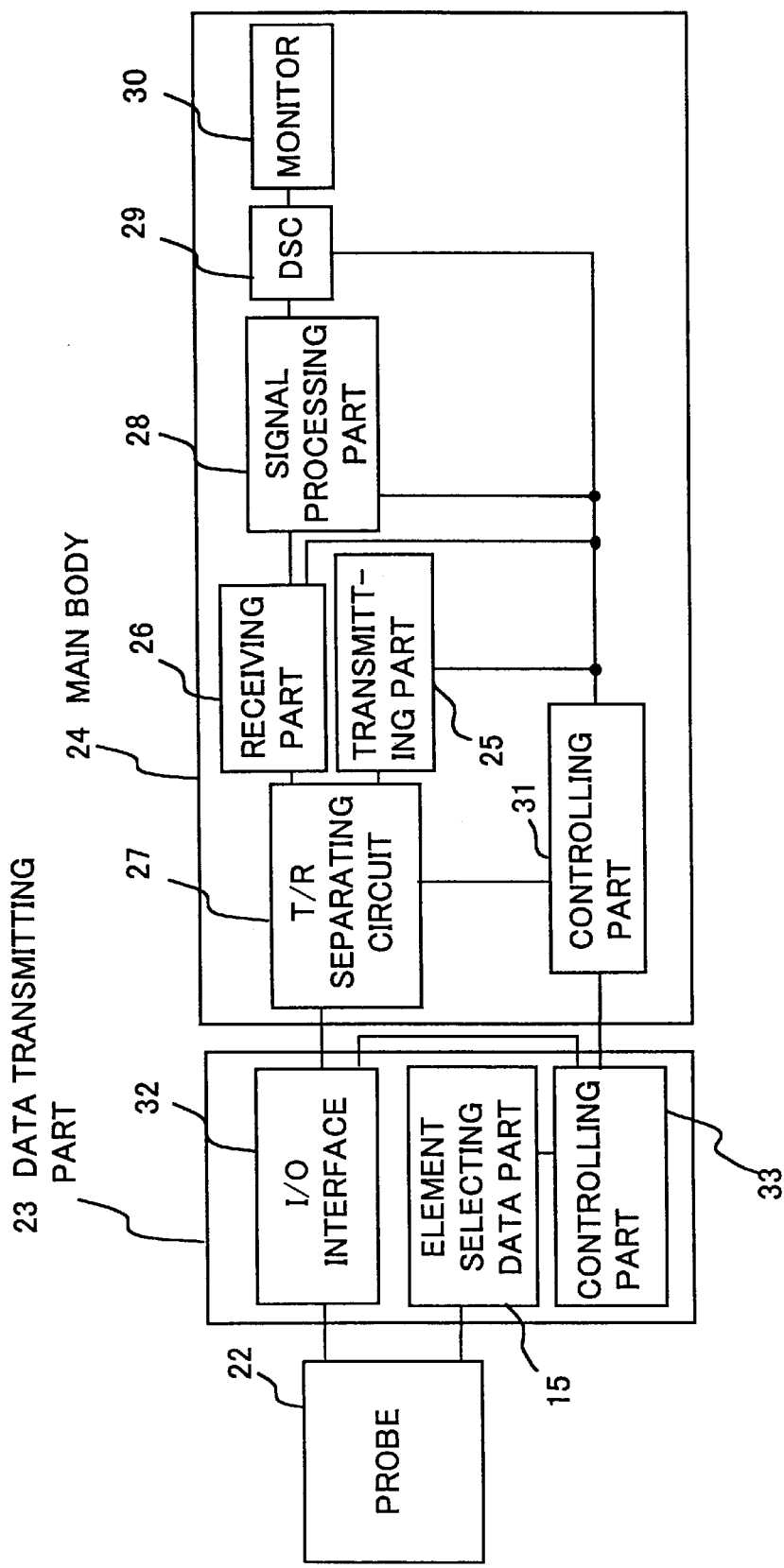
FIG. 7 is a block diagram showing an embodiment of the ultrasonic diagnostic apparatus in the related invention of the present invention.

FIG. 7 is a block diagram for showing an embodiment of ultrasonic diagnostic apparatus as a related invention of said first invention. This ultrasonic diagnostic apparatus gets and displays an ultrasonic image of diagnosis part in the interior of the object by using ultrasonic signals corrected with transmitting and receiving ultrasound to the object. And as shown in FIG. 7, it comprises probe 22, data transmitting part 23, and main body 24.

Said probe 22 transmits and receives ultrasound to the object to be examined. In the present invention, the ultrasonic probe of the first invention shown in FIG. 1 or FIG. 6 described above or the ultrasonic probe arranged two-dimensional array transducer on the plane are used for a probe 22.

In addition, main body 24 of diagnostic apparatus gets and displays an ultrasound image of diagnosis part in the interior of the object by using ultrasound signals corrected with said probe 22. And it is composed as same as that of the traditional ultrasonic diagnostic apparatus used in general. That is to say, main body 24 comprises transmitting part 25 for supplying a transmitting signal to the transducer elements with delay time by a transmitting delay circuit or a timing control such that a transmitted ultrasound from said probe to the object is focused to a desired focused point, receiving part 26 for forming a receiving beam signal by beam forming process about an echo signal received with said probe 22, transmitting and receiving separation circuit 27 for exchanging the connection of probe 22 to said transmitting part 25 or receiving part 26 corresponding to the ultrasound transmitting or receiving, and signal processing part 28 for performing a detection processing, a logarithm compression processing, an edge emphasis processing or the like by inputting a received signal from said receiving part 26, digital scan converter (DSC) 29 for forming an image data by inputting a data from this signal processing part 28, together performing a scan transformation and interpolation processing or the like for displaying an image, monitor 30 for displaying a data inputted from this DSC 29 as an ultrasonic image, and controlling part 31 including CPU for controlling an operation of said each units.

Furthermore, in the present embodiment, data transmitting part 23 is disposed between said probe 22 and main body 24. This data transmitting part 23 is connected between main body 24 and probe 22 to input and output a selecting data of transducer elements and said corrected ultrasound signal. And it comprises element selecting data part 15, in which an element selecting data is accommodated to form a diameter (hereinafter described) for transmitting and receiving by controlling element selecting switch 14 (refer to FIG. 5) disposed in the neighborhood of the transducer of ultrasonic probe shown in FIG. 1 and FIG. 6, and an input and output interface 32 for performing the transmitting and receiving of ultrasound by connection of probe 22 and main body 24, and control part 33 for controlling said element selecting data part 15 and input and output interface 32 so as to be possible transmitting and receiving ultrasound with the selected transducer elements.

Said control part 33 is also connected to controlling part 31 in main body 24. And, said element selecting data part 15 is comprised of, for example ROM (Read only memory), to memorize an element selecting data for forming a diameter of ultrasound transmitting and receiving. The data readout from element selecting data part 15 is transferred to shift register 16 as shown in FIG. 5. And switch on and off of element selecting switch circuit 14 are controlled so as to form a diameter of ultrasound transmitting and receiving through said shift register 16 and parallel latch 17 and decoder 18.

Figure 8:
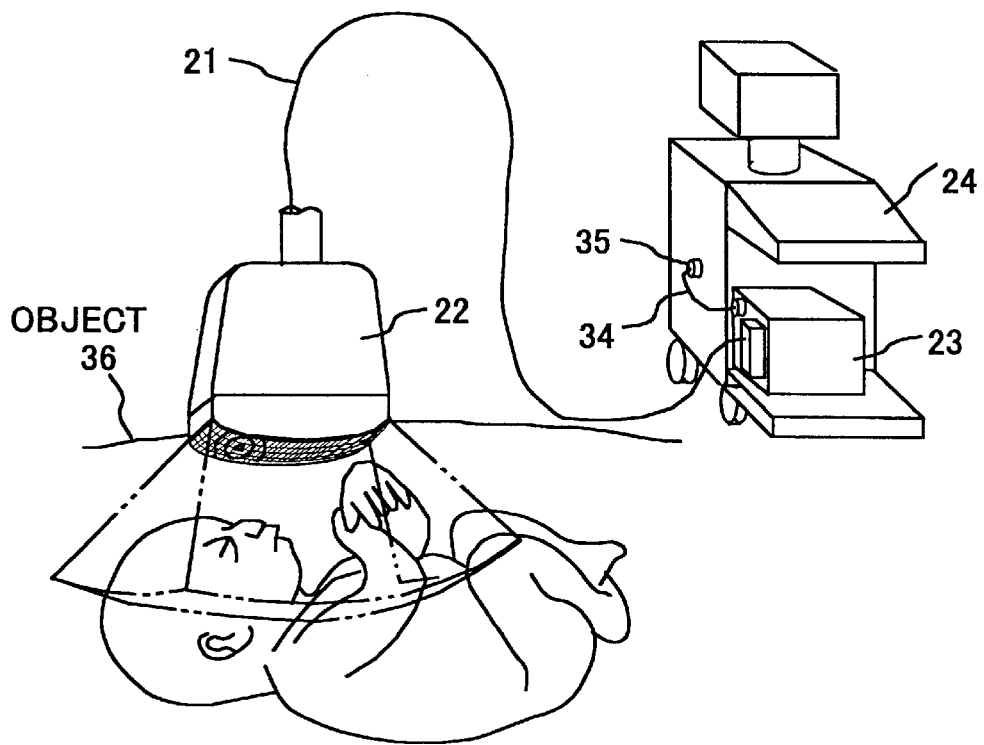
FIG. 8 is a view showing a use embodiment of ultrasonic diagnostic apparatus shown in FIG. 7.

FIG. 8 is an outline diagram showing an operating state of ultrasonic diagnostic apparatus shown in FIG. 7. That is to say, cable 21 stretched from the ultrasonic probe shown in FIG. 1 or FIG. 6 is connected to data transmitting part 23, and cable 34 stretched from this data transmitting part 23 is connected to connector 35 of main body 24. Probe 22 is contacted to the object to be examined 36. As described above, by lying data transmitting part 23 between probe 22 and main body 24, it is possible to connect the two-dimensional array probe to a traditional and general ultrasonic diagnostic apparatus without using an ultrasound diagnostic apparatus for an exclusive use of the two-dimensional array probe.

Figure 9:
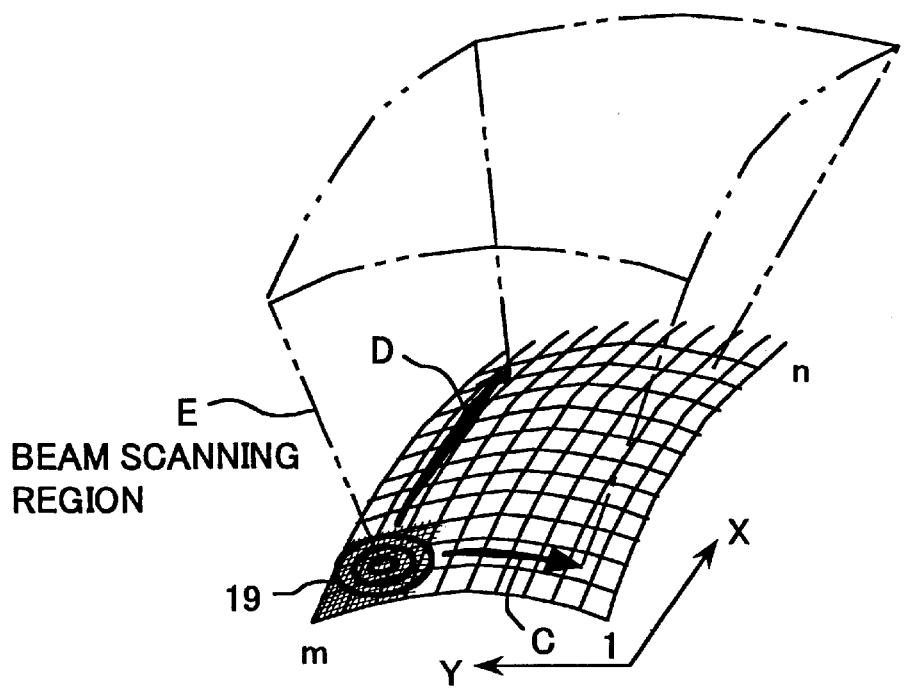
FIG. 9 is an operation diagram of three-dimensional scanning the object by an ultrasonic beam with selected diameter.

Next, one embodiment for ultrasound transmitting and receiving in said ultrasound diagnostic apparatus will be described. FIG. 9 shows a concept for three-dimensional scanning of the object to be examined. In FIG. 9, two-dimensional array transducer 1 has the sum of m×n transducer elements to the directions of X, Y being perpendicular to each other, n in X direction and m in Y direction, for example previously described 12,488 or 6,244 pieces. Transducer groups (diameter) 19 driven for transmitting and receiving in its array are formed. Diameter 19 is composed of plural number of concentric ring (fresnel ring). As a fresnel ring, for example, 32 concentric rings in which each ring has 64 transducer elements, or 16 concentric rings in which each ring has 58 transducer elements or the like can be raised. But number of ring and element forming one ring can be determined in accordance with system composition. To form each ring with the same number elements or with other reason, the width of ring is narrowed as it goes to the exterior. The reason will be described later.

This diameter 19 is moved in the direction of X or Y at each cycle of ultrasound transmitting and receiving, or C or D direction along the arrangement face of transducer with a predetermined order. And at each position of diameter in the moving process, ultrasound is transmitted from diameter 19 to the object to be examined, and the reflection wave is received. And as a result three-dimensional scanning is performed to the interior of the object with ultrasound beam.

Figure 10:
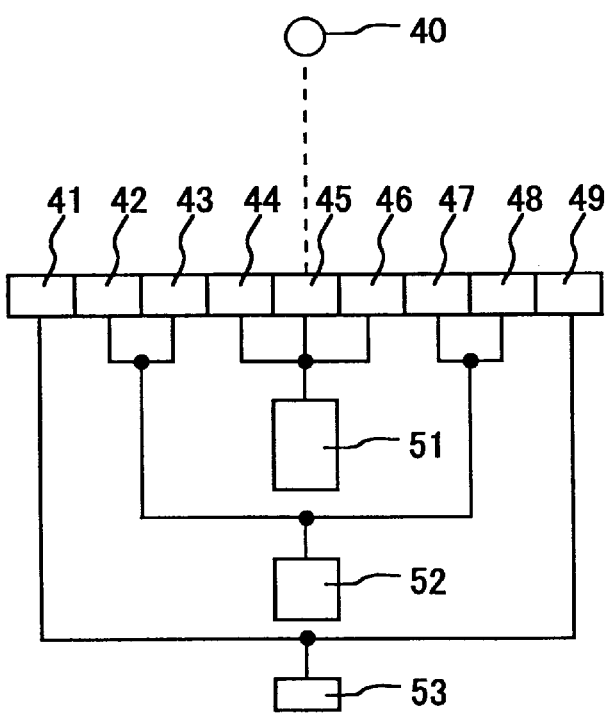
FIG. 10 is a view showing fresnel bundled connection of probe and delay circuit

FIG. 10 shows connection between transducer elements for transmitting and receiving and delay circuits in the two-dimensional array probe of the present invention. In FIG. 10, 41~49 are transducer elements, 51~53 are delay circuits, and 40 is a convergence point of ultrasound (focus point). Transducer element 44, 45, 46 form the first ring, and 42, 43 and 47,48 positioned in the exterior of them form the second ring, their radius are larger than the former. 41, 49 positioned in the further exterior of them form the third ring, which has the largest diameter. As thus described above, the ring width of outer ring is narrower than that of inner ring in order of the first ring, the second ring and the third ring. And in the actual device, number of ring is 32 or 16, and elements are divided with the idea as shown in FIG. 10.

And, transducer element 44, 45, 46 forming the first ring is connected commonly (bundling connection) to delay circuit 51. And transducer element 42, 43, 47, 48 forming the second ring is connected to delay circuit 52 with bundling, and transducer element 41, 49 forming the third ring is connected to delay circuit 53 with bundling. This reason for using this bundling connection method is to make the number of delay circuit less, and the device compact. In case this bundling connection is not used, the delay circuit and delay data are needed to each element composing fresnel ring. If fresnel ring is formed with 2,048 or 928 elements as thus described, the number of delay circuit and delay data are needed the number of them. Then the device becomes very large and cost is raised up with it.

Although one delay circuit is composed at each ring in FIG. 10, the main purpose shown in FIG. 10 is that transducer elements forming one ring are controlled with the same delay time for transmitting ultrasound and receiving signal. Accordingly it is preferable to arrange a delay circuit for applying the same delay time to signal at every region formed by dividing one ring to plural number of region. But in this case, it is apparent that number of delay circuit is less than number of elements for forming ring. In addition, it is preferable to change number of ring, number of delay circuit, connecting state shown in FIG. 10 with transmitting time and receiving time. The acoustic field of ultrasound transmitted from the transducer of fresnel ring has a narrow characteristics, so it is preferable that the delay control is performed to roughly divided ring in transmitting, and to finely divided ring in receiving.

Said ring forming and connecting of delay circuits is controlled with controlling part 31 and controlling part 33. Controlling part 31 controls an ultrasound transmitting and receiving and an image forming and displaying in the whole ultrasonic diagnostic apparatus. Controlling part 33 receives an ultrasound transmitting and receiving commands and a scanning commands from controlling part 31, and controls the selection of transducer elements serving an ultrasound transmitting and receiving, and the connection of transducer elements and delay circuits. Controlling part 33 receives the commands from controlling part 31 at each cycle of transmitting and receiving, and sends the transducer element selecting commands to element selecting data part 15 for performing the next transmitting and receiving. Corresponding to this transducer element selecting commands, the signals for forming fresnel ring and the signals for performing connection changes of fresnel ring and delay circuit are output from element selecting data part 15 to element selecting switch circuit 14.

Selecting switch circuit 14 has m×n×s switching elements in case that two-dimensional probe 22 has m×n elements and selecting switch circuit has s input and output lines. And if the number of transducer forming whole fresnel ring is F, and each ring has the same number of transducer, and number of ring is N, then input and output line number to selecting switch circuit 14 is N. And one of N is connected to one ring having transducer elements of F/N. In addition, a connecting end of input and output line from selection switch circuit 14 is transmitting delay circuit in transmitting part 26, or beam forming circuit in receiving part 25. Its number is the same as transmitting and receiving channel number being able to control independently in the main body. Generally it is multiplier of 2 and more than 16.

Transmitting delay circuits sets an ultrasound focus depth in the object to be examined when ultrasound is transmitted. Beam forming circuit moves dynamically focusing depth at signal receiving (this is called dynamic focusing) and adds signals output from each channel with making them a same phase. For example, a delay time data applied to transmitting delay circuit is set with the apparatus corresponding to predetermined depth in region of interest (ROI) of the object input by an operator. And the delay time data for moving focus point is given automatically with the apparatus to overall depth for measuring signal to the delay circuit in beam forming circuit.

These delay time data are calculated by calculations based on the distance value determined with geometrical arrangements of transducer elements and focus points, or is previously accumulated and accommodated in ROM of controlling part 31.

Hereinafter the operation of ultrasonic diagnostic apparatus shown in FIG. 7 will be described. An operator makes contact probe 22 with the examined part of the object. And an operator inputs an ultrasound scanning commands to main body 24, and then controller 31 sends an ultrasound scanning beginning commands to each unit. Controlling part 33 received this commands outputs an element selecting commands for performing the first ultrasound transmitting and receiving to element selecting data part 15. Corresponding to this commands, on/off commands of each switch in element selecting switch circuit 14 are output from element selecting data part 15. The transducer elements serving the first transmitting and receiving in probe 22 are selected with on/off operation of each switch at element selecting switch circuit 14. Selected transducer elements form said fresnel ring. And transducer elements forming each ring of this fresnel ring are connected with bundling. When this connection is completed, the transmitting pulse signals are output from transmitting part 25. Transmitting pulse provided delay time respectively is applied to each fresnel ring. Transmitting pulse is guided to an input and output line of interface 32 by transmitting and receiving separation circuits 27 and provided to each ring of two-dimensional probe 22. Thus focused ultrasound is irradiated to predetermined depth in the object from probe 22.

Figure 11:
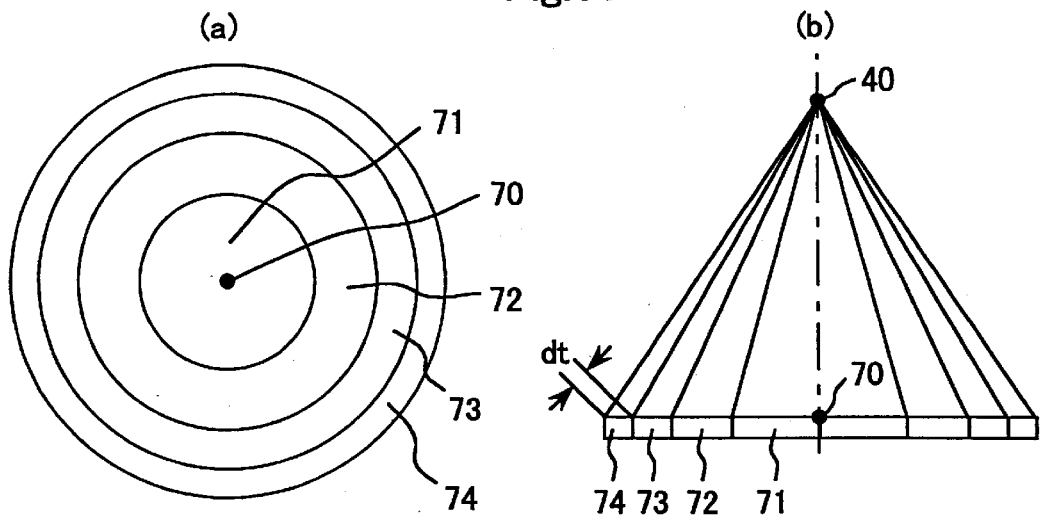
FIG. 11 is a view showing ultrasound transmitting by fresnel bundling.

Here, the forming method of fresnel ring when a transmitting wave is focused will be described referring to FIG. 11. In FIG. 11, 70 is a center of fresnel ring, 71, 72, 73, 74 are fresnel ring formed with plural number of transducer element. The Exterior circle of fresnel ring 74 is diameter 19. Then the relationship between radius of ring and focus point is explained. In this all fresnel ring, in case transmitting focus point 40 is located deeper than 50 mm in the object, it is preferable such that difference dt between a maximum and a minimum value of distance, which is distance between transmitting focus point 40 and transducer element in each ring, is less than ½ wave length of ultrasound emitted from the probe, or more preferably less than ⅛ wave length of ultrasound of the probe. For example, the reason is that when dt is ½ wave length, phase of comrade ultrasound differ about 180 degrees. Then ultrasonic wave is canceled with the comrade. As the best region being able to allow the influence of this canceling, said distance is selected less than ⅛ wave length. In addition, when depth of transmitting focus point 40 is needed to be set less than 50 mm, for example in case of the examination of carotid artery, value of dt may be more than ⅛ without changing the diameter. In this case, it is preferable to make small the diameter by changing the width of each ring without changing ring number of fresnel ring for transmitting. Or it is preferable to make narrow the diameter substantially by driving only rings satisfying said condition in center part. Moreover, it is preferable such that signal is received with said small diameter until the depth that value of dt is more than ⅛ wave length, and when it is deeper than that, signal is received with said larger diameter. In the present invention, consistent delay time controlling is performed to each ring, so ultrasonic beam is formed to perpendicular direction on the ultrasound transmitting surface. From the setting method of said value dt, fresnel rings 71 is concentric circle with the center of diameter. And the width of exterior concentric ring becomes narrower.

Figure 13:
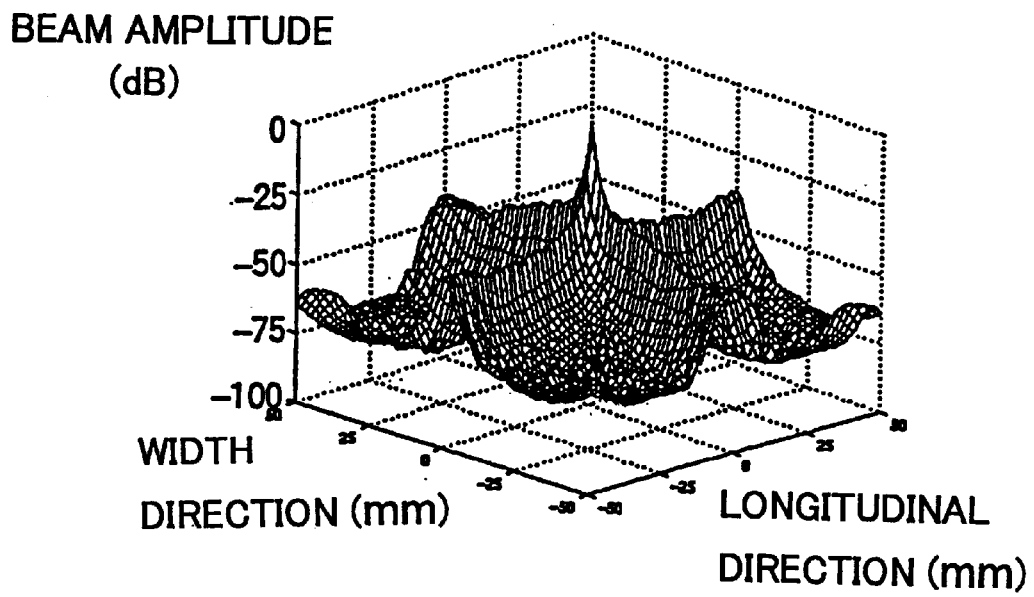
FIG. 13 is a beam simulation view inspecting effectiveness of fresnel bundling in the present invention.
Figure 13:
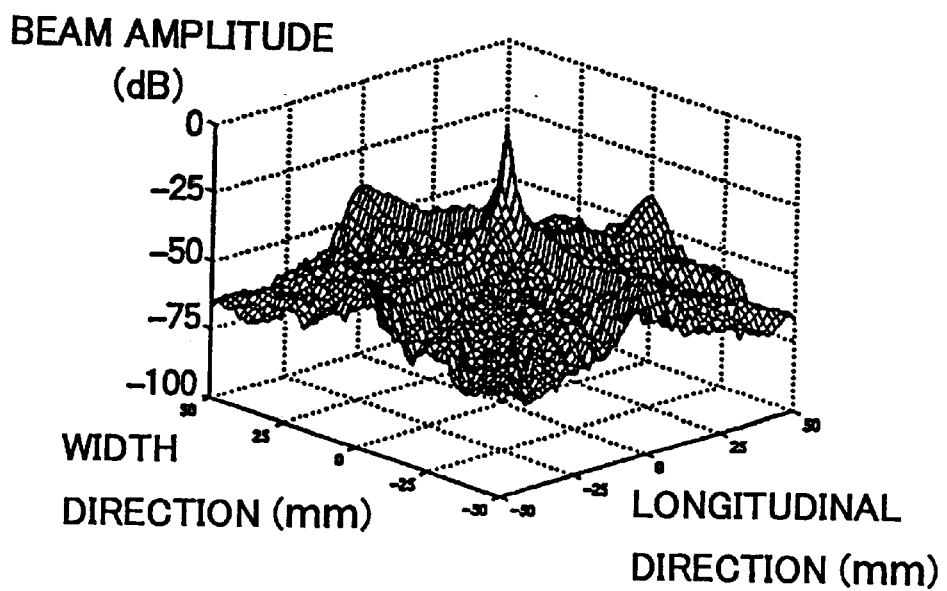

Next the validity that difference between a maximum value and a minimum value of distance, which is distance between transducer element and focus point in each ring, is made to be less than $\frac{1}{8}$ wave length will be explained referring to FIG. 13. FIG. 13 shows the beam amplitude (sound pressure) of two-dimensional ultrasound beam calculated by simulation at depth 50 mm when the focus point is located 50 mm in front of diameter by using the two-dimensional convex type probe formed ultrasound transmitting and receiving face convexly at both directions, in which an ultrasound frequency is 3.5 MHz, a curvature radius in longitudinal direction is 40 mm, a curvature radius in width direction is 25 mm, and an element pitch is 0.38×0.38 mm. In addition, the diameter used for this simulation has 64 elements in longitudinal direction, and 32 elements in width direction.

FIG. 13(*a*) shows the ideal beam in case delay controlling is performed to all of 2,048 elements of diameter. FIG. 13(*b*) is an amplitude distribution figure of beam when the diameter is divided to 32 fresnel rings and delay controlling is performed with fresnel bundling. The latter fresnel bundling is performed such that difference between a maximum and a minimum of distance, which is distance between element of ring and focus point, is made to be less than $\frac{1}{8}$ wave length. Comparing with two figures, the main beam width of the latter is the same as ideal beam in the former, and the useless response is less than minus 40 dB. Accordingly it will be no problem in practical use.

Next, receiving operation will be described. When ultrasound was transmitted from ultrasound probe 22 to the object, controlling part 31 sends commands of receiving operation. And ultrasound transmitted from ultrasound probe 22 to the object reflects at boundary where acoustic impedance in the object is different. The reflecting signal is received with the same two-dimensional probe 22. At this time, element selecting data part 15 holds the data that is used in transmitting. Accordingly fresnel ring as same as signal transmitting is formed in probe 22. In addition, as thus described, when signal is received, the form of fresnel ring (ring number, number of element for forming one ring and diameter) can be changed.

Figure 12:
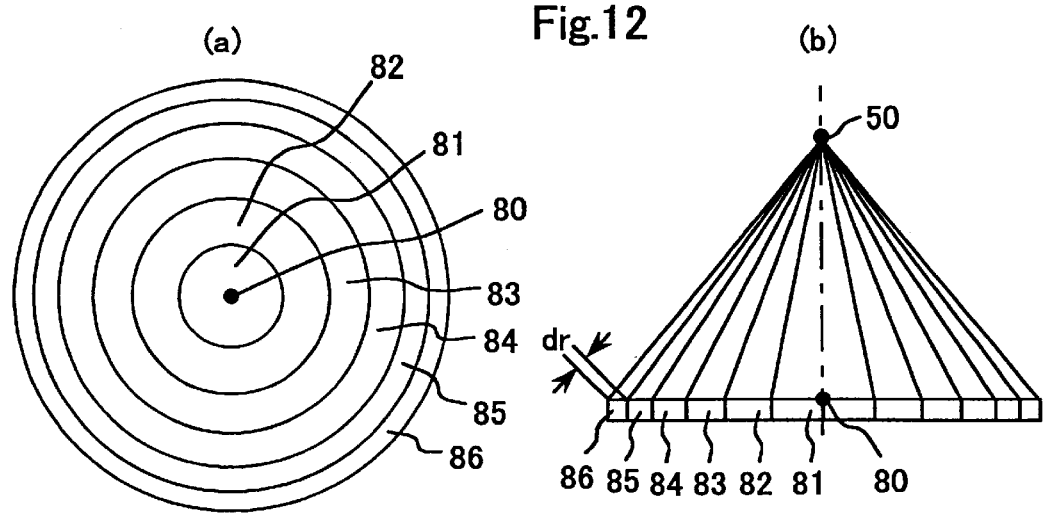
FIG. 12 is a view showing ultrasound receiving by fresnel bundling.
Figure 12:
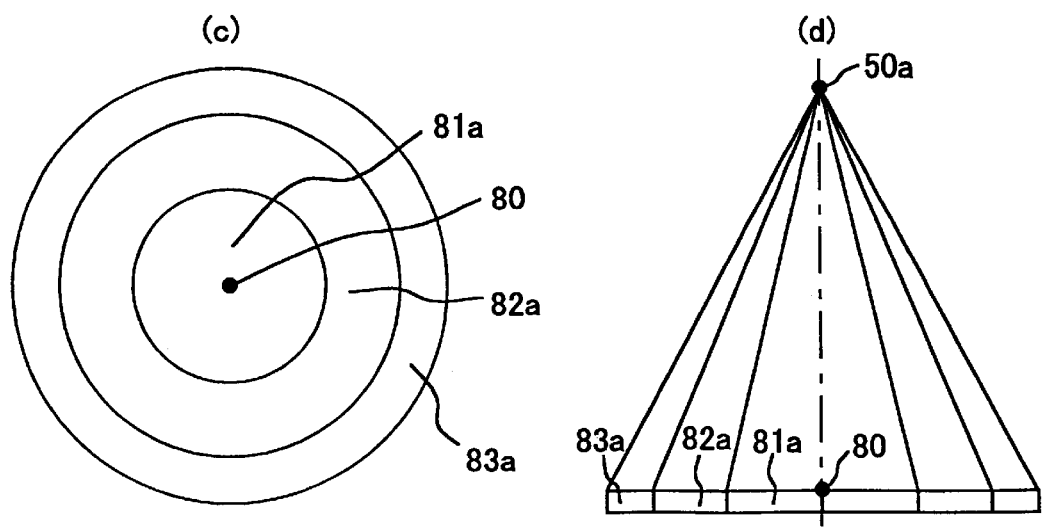

Then an example to modify the form of frensel ring in comparison with transmitting will be described. Although in the present invention the dynamic focusing is performed when signal is receiving, it is preferable to form the fresnel ring at the dynamic focusing as shown in FIG. 12. In FIG. 12(*a*), 80 is a center of fresnel ring at receiving, 81, 82, 83, 84, 85, 86 are fresnel ring, 50 is a receiving focus point. The exterior circle of fresnel ring 86 is a receiving diameter. And as shown in FIG. 12(*b*), it is preferable such that difference dr between a maximum value and a minimum value of distance, which is distance between receiving focus point 50 and element in one ring, is less than certain value as same as the transmitting case, preferably less than $\frac{1}{8}$ wave length of ultrasound, also in fresnel ring of receiving.

In the present invention, same delay time controlling is performed at each ring in receiving too, so ultrasonic beam is formed on perpendicular line that passes through the center of fresnel ring 80. Accordingly, when focus point 50 changes from short distance to long distance, the fresnel ring is maintained a concentric circle with the center of ultrasound receiving diameter. When the focus point is closer to the ultrasound receiving face, the distance between element and focus point is lager. As the method for dealing with this, in case focus point 50 is close to the face, the fresnel ring can be composed with a concentric ring having relatively narrow width as shown in FIGS. 12(*a*),(*b*). And in case the focus point is located at 50*a* with long distance, the fresnel ring can be composed with a concentric ring having small number of ring and relatively wide width comprised of 81*a*, 82*a*, 83*a* as shown in FIGS. 12(*c*), (*d*). Moreover it is preferable to receive only with the central part when focus point 50 is at close distance, and to increase the number of ring in accordance with focus point 50 becomes larger distance. That is to say, it is preferable to apply a variable diameter method. Furthermore, it is preferable to modify the shape of fresnel ring between a closing distance region and a long distance region of focus point, and to divide each region to scan. It is preferable to combine with each echo signals acquired separately for imaging.

Furthermore in other embodiment, it is preferable to fix the fresnel ring with a close distance pattern as shown in FIGS. 12(*a*),(*b*) during receiving dynamic focusing. Fixing the fresnel ring with a close distance pattern, when it is used for a long distance, the difference between a maximum distance and a minimum distance, which is distance between focus point and element in each fresnel ring, becomes small in comparison with a short distance case. For example in certain fresnel ring, if the difference dr between a maximum and a minimum value between focus point and element at close distance is $\frac{1}{8}$ wave length, at a long distance the difference dr will be for example $\frac{1}{16}$ wave length of ultrasound. Accordingly an accuracy of delay to signal is improved in comparison with the case of short range. That is to say, ultrasonic beam does not deteriorate at long distance focusing.

In addition, in case channel number of beam forming circuit disposed in receiving part 26 is little, if the fresnel ring is fixed in the pattern for short range, sometimes the width of fresnel ring becomes narrow and the diameter is small. In this case, it is necessary to define a fitting pattern of fresnel ring with the consideration of both difference dr between a maximum and a minimum of distance between focus point and element in each fresnel ring and diameter.

Hereinafter, moreover the receiving operation will be described. Starting receiving operation, controlling part 31 supplies successively focusing data to all of the beam forming circuit to perform the dynamic focusing in receiving part 26 so as to continuously move the receiving focus point from shallow part to deep part of the object to be examined. Thus echo groups received with fresnel ring are aligned their phase with beam forming circuit, and output as ultrasonic beam signal (echo signal) with addition circuit. And signal processing part 28 performs detection processing, logarithm compression, filtering processing, edge emphasis processing or the like to output signal and sends processed signals to DSC 29. DSC 29 converts input signals to digital signals, thereafter writes them to memory build in it. By above-mentioned operation, the first ultrasound transmitting and receiving operation is completed.

Next, controlling part 31 sends the second ultrasound transmitting and receiving commands to each unit. Although the first transmitting and receiving is performed at position shown in FIG. 9, this second transmitting and receiving is performed by forming fresnel ring at position moved a predetermined distance to a certain direction of X or Y direction. And a received echo signal is written in said memory in DSC 29 as same as the first transmitting and receiving. After this, the position of fresnel ring on the probe is moved similarly to said predetermined direction consecutively, and two-dimensional scanning is performed in the object with ultrasonic beam. And when this two-dimensional scanning was completed, one slice image of the object is formed in memory of DSC 29. Controlling part 33 reads out said slice image data in memory of DSC 29 in synchronization with horizontal scanning for displaying on monitor. The slice image is displayed on display screen in monitor 30. After said two-dimensional scanning was completed, controlling part 31 performs two-dimensional scanning again with moving fresnel ring on probe from the position in said two-dimensional scanning to different position in this scanning. With this repetition, beam scanning region E in the object to be examined as shown in FIG. 9 is scanned three-dimensionally with ultrasonic beam. With this three-dimensional scanning, plural numbers of slice data are acquired to accommodate to the memory in DSC 29. And those slice image data are three-dimensionally image processed with three dimensional image reconstruction method such as surface rendering method or volume rendering method etc. by controlling part 33 to display screen of monitor 30 as a three dimensional image. Diagnosis to use this ultrasonic three-dimensional image involves a deformity diagnosis of an unborn baby before birth at obstetrics and gynecology department or the like. It will be understood that a modified example is possible, and it is preferable to perform image processing for forming a three-dimensional image with image processing device composed separately from a main body.

Furthermore, in a setting method of diameter shown in FIG. 9, all of fresnel ring moved are set so as to draw perfect circle at the end of ultrasonic probe. But in this method, the ultrasonic beam in most outer edge is interior of outline of transducer arrangement face of probe with radius of fresnel ring. So a scanning region of ultrasonic beam is small. To solve this problem, when the ultrasonic beam in most outer edge is transmitted and received in three-dimensional scanning with the present probe, it is preferable to form an imperfect fresnel ring, for example fresnel ring of ½ circle and to locate ultrasonic beam to the edge of transducer array.

According to the second invention of the present invention previously described, by using data transmitting part between probe and main body, three-dimensional scanning can be performed with ultrasonic beam to the object with connecting said ultrasonic probe in said the first invention to traditional and general ultrasonic diagnostic apparatus without using ultrasonic diagnostic apparatus for only two-dimensional array probe.

In addition, according to the ultrasonic diagnosis device of the present invention, ultrasonic beam is usually perpendicular to ultrasonic transmitting and receiving face and formed in the center of fresnel ring. So in case location of focus point is changed from short distance to long distance, form of fresnel ring need not be changed. This is a characteristic of the present invention. The element bundling in processing of received signal is not needed. So both of fresnel bundling and receiving dynamic focusing can be performed. And receiving dynamic focus can easily be performed.

What is claimed is:

1. An ultrasonic probe comprising:
   a plural number of transducer base members, each of which has: a plural number of transducer elements arranged in a first direction with a first convex shape for ultrasound transmitting and receiving, and a plural number of switching members for selecting ones of the plural number of transducer elements;
   wherein said plural number of transducer base members are arranged in a second direction transverse to the first direction, to form a convex shape in the second direction.

2. An ultrasonic probe as claimed in claim 1, comprising:
   an element selecting switch circuit for selecting ones of the transducer elements for performing transmitting and receiving an ultrasound.

3. An ultrasonic probe as claimed in claim 2, wherein said element selecting switch circuit has an output line for selecting to each transducer element, input lines less in number than a total number of arranged transducer elements, and a control line for inputting a control signal for performing transducer selecting change.

4. An ultrasonic probe as claimed in claim 2, wherein a control signal given to said element selecting switch circuit selects arbitrary transducer elements from a two-dimensional array of the plural number of transducer elements to form an activated-transducer probe of a predetermined diameter for ultrasound transmitting and receiving, and said activated-transducer probe is movable to an arbitrary position in the two-dimensional array at each ultrasound transmitting and receiving cycle.

5. An ultrasonic probe as claimed in claim 4, wherein said activated-transducer probe is moved in two directions of the two-dimensional array in a predetermined order.

6. An ultrasonic probe as claimed in claim 1, wherein the transducer elements arranged in the two-dimensional array are arrayed in a radial direction in one direction of arrangement, and also in another direction.

7. An ultrasonic probe as claimed in claim 6, wherein an ultrasonic transmitting and receiving face of the ultrasonic probe is formed convexly with a radius of substantially 60 mm and with a circular angle of substantially 68 degrees in one direction of arrangement, and in another direction with a radius of substantially 32 mm and with a circular angle of substantially 48 degrees.

8. An ultrasonic probe as claimed in claim 1, wherein each transducer element arrayed two-dimensionally is arrayed radially in one direction, and arrayed parallel along a center axis of a circle in another direction.

9. An ultrasonic probe as claimed in claim 8, wherein said ultrasound transmitting and receiving face of the ultrasonic probe is arrayed radially with a diameter of substantially 60 mm and with a circular angle of substantially 68 degrees.

10. An ultrasonic probe comprising:
    a plural number of transducer base members, each of which has: a plural number of transducer elements arranged in a first direction for ultrasound transmitting and receiving, and a plural number of switching members for selecting ones of the plural number of transducer elements;
    wherein said plural number of transducer base members are arranged in a second direction transverse to the first direction;
    wherein said plural number of transducer elements is arrayed convexly to an ultrasound transmitting direction at least in one direction of the two dimensional array.

11. An ultrasonic probe as claimed in claim 10, comprising:
    an element selecting switch circuit to select arbitrary transducer elements from a two-dimensional array of the plural number of transducer elements to form an activated-transducer probe of a predetermined size for ultrasound transmitting and receiving, wherein the predetermined size is smaller than a length of both sides of the two-dimensional array.

12. An ultrasonic diagnostic apparatus comprising;

an ultrasonic probe having ultrasonic transducer elements in a two-dimensional array, by having a plural number of transducer base members, each of which has: a plural number of transducer elements arranged in a first direction for ultrasound transmitting and receiving, and a plural number of switching members for selecting ones of the plural number of transducer elements; wherein said plural number of transducer base members are arranged in a second direction transverse to the first direction;

an element selecting means for selecting ones of the transducer elements of the two-dimensional array to perform transmitting and receiving of ultrasound;

bundling means for supplying a bundling data to said element selecting means for bundling and connecting ones of the transducer elements to predetermined transducer groups;

delay means for controlling ultrasound to an object with predetermined transmitting delay time to each transducer group of the predetermined transducer groups;

beam forming means for beam forming each receiving signal output from said each bundling group of the predetermined transducer groups;

imaging means for image processing an output signal of said beam forming means, and an image display means.

13. An ultrasonic diagnostic apparatus as claimed in claim 12, wherein at least one bundling group of the predetermined transducer groups form a fresnel ring of concentric circles.

14. An ultrasonic diagnostic apparatus as claimed in claim 13, wherein a difference of a maximum and a minimum distance between transducer elements forming a fresnel ring in each ring and an ultrasonic focus point, is less than a ⅛ wavelength of the ultrasound.

15. An ultrasonic diagnostic apparatus as claimed in claim 13, comprising means for controlling said beam forming means such that a receiving focus point is moved continuously on a center line of said fresnel ring without changing a form of said fresnel ring in a receiving period of an echo signal.

16. An ultrasonic diagnostic apparatus as claimed in claim 13, comprising means for changing a form of said fresnel ring corresponding to a depth of a receiving focus point.

17. An ultrasonic diagnostic apparatus as claimed in claim 16, comprising means for scanning a predetermined region of depth within the object at each form of said fresnel ring, and for composing an image from an echo signal acquired at each region of depth.

18. An ultrasonic diagnostic apparatus comprising:

a two-dimensional array probe for transmitting and receiving ultrasound to an object, the two-dimensional array probe having a plural number of transducer base members, each of which has: a plural number of transducer elements arranged in a first direction for ultrasound transmitting and receiving, and a plural number of switching members for selecting ones of the plural number of transducer elements; wherein said plural number of transducer base members are arranged in a second direction transverse to the first direction;

a diagnostic apparatus for acquiring and displaying an ultrasonic image of a desired diagnosis part in an interior of the object by using an ultrasonic signal with said two-dimensional array probe, a data transmitting part for inputting and outputting both a selecting data for selecting transducer elements and said ultrasonic signal, between said two-dimensional array ultrasonic probe and said diagnostic apparatus.

* * * * *